(12) United States Patent
Tseng et al.

(10) Patent No.: US 10,016,170 B2
(45) Date of Patent: Jul. 10, 2018

(54) LOADING MECHANISM FOR X-RAY TUBE AND SCANNING SYSTEM FOR THREE-DIMENSIONAL IMAGING

(71) Applicant: Institute of Nuclear Energy Research, Atomic Energy Council, Executive Yuan, R.O.C., Taoyuan (TW)

(72) Inventors: Sheng-Pin Tseng, Taoyuan (TW); Ho-Hui Hsieh, Taoyuan (TW)

(73) Assignee: INSTITUTE OF NUCLEAR ENERGY RESEARCH ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 300 days.

(21) Appl. No.: 15/133,682

(22) Filed: Apr. 20, 2016

(65) Prior Publication Data

US 2017/0125198 A1 May 4, 2017

(30) Foreign Application Priority Data

Oct. 28, 2015 (TW) .............................. 104135452 A

(51) Int. Cl.
*A61B 6/00* (2006.01)
*A61B 6/02* (2006.01)
*G01V 5/00* (2006.01)

(52) U.S. Cl.
CPC ............... *A61B 6/00* (2013.01); *A61B 6/025* (2013.01); *A61B 6/4021* (2013.01); *G01V 5/00* (2013.01)

(58) Field of Classification Search
CPC .................................................... A61B 6/4021
See application file for complete search history.

(56) References Cited

U.S. PATENT DOCUMENTS

| 2004/0240609 | A1* | 12/2004 | Spahn | A61B 6/488 |
| | | | | 378/63 |
| 2007/0140435 | A1* | 6/2007 | Schwieker | A61B 6/4464 |
| | | | | 378/193 |

\* cited by examiner

*Primary Examiner* — Dani Fox
(74) *Attorney, Agent, or Firm* — Locke Lord LLP; Tim Tingkang Xia, Esq.

(57) ABSTRACT

The invention provides a loading mechanism for x-ray tube. The loading mechanism for x-ray tube includes an x-ray tube, a swing element and a rotating element. The x-ray tube includes a focal spot location and an x-ray opening. The swing element includes a first rotating axis, and the first rotating axis passes through the focal spot location. The swing element rotates about the first axis to rotate the x-ray tube within a limit swing range. The rotating element is connected to the swing element. The rotating element has a second rotating axis, and the first rotating axis perpendicular to the second rotating axis. The rotating element rotates about the second rotating axis to drive rotate the x-ray tube and the swing element. In addition, the scanning system for three-dimensional image is provided.

16 Claims, 3 Drawing Sheets

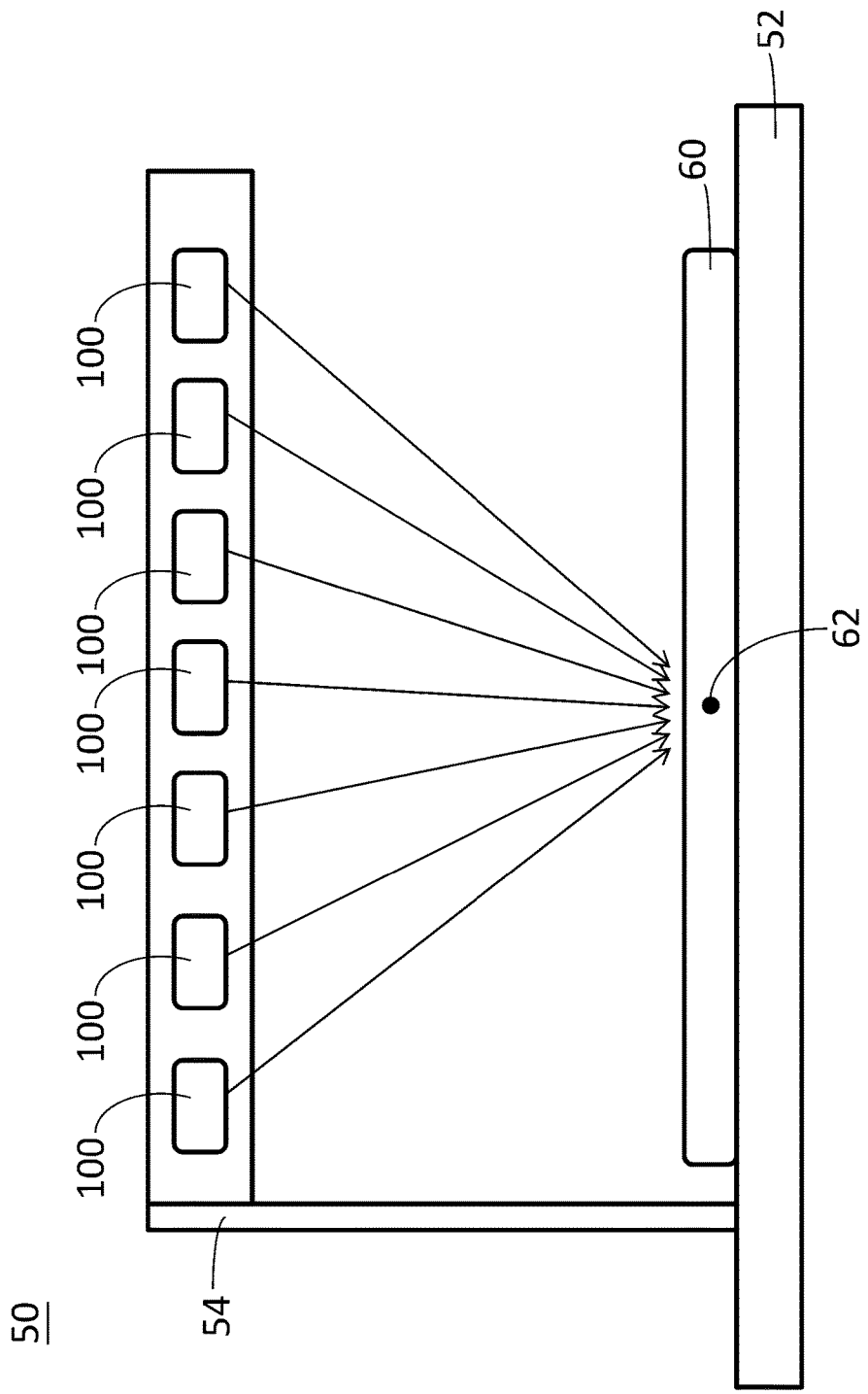

LOADING MECHANISM FOR X-RAY TUBE AND SCANNING SYSTEM FOR THREE-DIMENSIONAL IMAGING

CROSS REFERENCE TO RELATED APPLICATION

This application also claims priority to Taiwan Patent Application No. 104135452 filed in the Taiwan Patent Office on Oct. 28, 2015, the entire content of which is incorporated herein by reference.

FIELD OF THE INVENTION

The present invention relates to a swing/rotating device, and more particularly, to a device capable of enabling an x-ray tube to swing and rotate from limited angle in complex direction for three-dimensional imaging.

BACKGROUND OF THE INVENTION

In recent years, x-ray radiography had been actively used in a wide variety of fields, such as the applications in medicine field, industrial field, home security field and agricultural field, etc. In the field of medicine, there are three main demands, namely a two-dimensional (2D) imaging, a temporal-dynamic fluoroscope imaging and a three-dimensional (3D) imaging, and the medical instruments being used in those applications include medical x-ray imaging devices, medical fluoroscopy and three-dimensional computed tomography. It is noted that the two-dimensional (2D) imaging and the temporal-dynamic fluoroscope imaging are used primarily for generaying two-dimensional planar images for medical evaluation. Taking a 2D x-ray process for chest anterior/posterior view imaging for example, the so-acquired planar images lack depth information so that the organs in the chest may appear overlapped on each other in the x-ray images, resulting in illegible fine structures. Therefore, it is difficult to interpret the planar x-ray images for identifying whether a lesion is located in front or behind the heart, mediastinum, diaphragm, vertebralis, etc. On the other hand, the 3D imaging, such as the CT scan, is performed using the x-ray sources and detectors that are arranged concyclically and surrounding a patient so as to generate a number of successive slices of cross-sectional image of the patient that can be then collected and digitally "stacked" together to form a three-dimensional image of the patient for medical interpretationa and abnormality identification. Despite that CT scan is able to provide generate a number of successive slices of cross-sectional image of the patient for forming a three-dimensional image of the patient, its high cost and high-dose risk cause the CT scan to be used only as a second-line inspection tool in medical diagnosis. According to the Report no. 160 on population exposure released by the National Council on Radiation Protection and Measurements (NCRP) in 2006, Americans were exposed to more than seven times as much ionizing radiation from medical procedures as was the case in the early 1980s, i.e. from 3.1 mSv at 1980s to about 5.5 mSv at 2006. The report further indicates that The increase was primarily a result of the growth in the use of medical imaging procedures, as such exposure of medical imaging procedures had grown 6 times from 0.5 mSv to 3.0 mSv with the 25-year period which is positively proportional to the growing prevalence of x-ray devices and CT scan in American. Therefore, it is reasonable to assume the increase was due mostly to the higher utilization of computed tomography (CT) and nuclear medicine. Consequently, the recent focal point in radiographic technology is committed to minimize the risk of radiation dose without sacrificing the quality of the three-dimensional images and the resulting medical benefits.

In additional to the aforesaid 2D imaging and CT imaging, a new technique, i.e. digital tomosynthesis, had been developed recently, which is a method for performing high-resolution limited-angle tomography at radiographic dose levels. Digital tomosynthesis combines digital image capture and processing with simple tube/detector motion as used in conventional computed tomography (CT). However, though there are some similarities to CT, it is a separate technique. In CT, the source/detector makes at least a complete 180-degree rotation about the subject obtaining a complete set of data from which images may be reconstructed. Digital tomosynthesis, on the other hand, only uses a limited rotation angle with a lower number of discrete exposures than CT. This incomplete set of projections is digitally processed to yield images similar to conventional tomography with a limited depth of field. Because the image processing is digital, a series of slices at different depths and with different thicknesses can be reconstructed from the same acquisition. However, since fewer projections are needed than CT to perform the reconstruction, radiation exposure and cost are both reduced. Moreover, the method of digital tomosynthesis can be performed using the current medical x-ray imaging devices with some improvement, so that it is possible to fulfill the abovementioned three main imaging demands in the field of medicine in one x-ray imaging device.

However, due to the limited angle scanning design that is used in the conventional digital tomosynthesis, the 3D imaging to an internal object with directional structure may not be satisfactory. Experimentally when a digital tomosynthesis device with limited angle scanning design adopts a longitudinal-direction scanning arrangement that is similar to the conventional medical x-ray device, the loading mechanism for the x-ray tube in the digital tomosynthesis device is driven to move along the longitudinal direction of its image table for scanning and imaging so that the the moving direction of the loading mechansim is parallel to the growing direction of human carotid arteries, and thereby the so-obtained 3D images of the carotid arteries can be clear for identification. On the other hand, if the aforesaid digital tomosynthesis devie is used for imaging a possible skull fracture while the cracking direction of the skull fracture is orientated different from the moving direction of the forgoing loading mechanism, the so-obtained 3D imaging of the skull fracture may not be clear enough. Therefore, for scanning a skull fracture, it is preferred to had the loading mechanism to move translationally, i.e. the loading mechansim is enabled to move translationally and thus is moving perpendicularly to the forgoing longitudinal direction, so that the translational moving direction is able parallel to the cracking direction of the skull fracture for allowing a clear imaging of the skull fracture. Generally, the clearness of a 3D imaging obtained from a digital tomosynthesis device with limited angle scanning design can be greatly affected by the directional structure in the object to be scanned, and can be improved if the scanning direction is about parallel to the orientation of the directional structure in the object. Nevertheless, as the direction of growth for most tissues and organs in human body, such as human skeleton, airway structure and blood vessel, can be very complex, the conventional unidirectional scanning design is not sufficient for satisfying the needs for scanning different human portions.

SUMMARY OF THE INVENTION

The present invention provides a loading mechanism for x-ray tube that is able to perform a digital tomosynthesis process in a longitudinal direction, in a translational direction, in an oblique direction or in a complex direction under a limited angle.

The present invention provides a scanning system for 3D imaging with an improved loading mechanism for x-ray tube, capable of being adapted for a digital tomosynthesis process in a complex direction as the degree of difficulty of the 3D spatial orientation is reduced.

The present invention provides a loading mechanism for x-ray tube. The loading mechanism for x-ray tube includes an x-ray tube, a swing element and a rotating element. The x-ray tube includes a focal spot location and an x-ray opening, and the focal spot location is related to a position where an x-ray beam is generated while the x-ray opening is located for allowing the x-ray beam to travel therethrough. The swing element is coupled to the x-ray tube and is composed of a first rotating axis in a manner that the first rotating axis is arranged passing through the focal spot location for allowing the swing element to rotate around first rotating axis while centering to the focal spot location and thus enabling the x-ray tube to swing within a limit swing range. The rotating element is connected to the swing element and is composed of a second rotating axis that is disposed perpendicular to the first rotating axis while enabling the rotating element to rotate about the second rotating axis so as to drive the x-ray tube and the swing element to move accordingly.

The present invention provides a scanning system for 3D imaging, which comprises: an imaging table and at least one loading mechanism for x-ray tube. The imaging table is provided for supporting an object to be imaged while the object is defined with a focal point. The loading mechanism for x-ray tube includes an x-ray tube, a swing element and a rotating element. The x-ray tube includes a focal spot location and an x-ray opening, and the focal spot location is related to a position where an x-ray beam is generated while the x-ray opening is located for allowing the x-ray beam to travel therethrough. The swing element is coupled to the x-ray tube and is composed of a first rotating axis in a manner that the first rotating axis is arranged passing through the focal spot location for allowing the swing element to rotate around first rotating axis while centering to the focal spot location and thus enabling the x-ray tube to swing within a limit swing range. The rotating element is connected to the swing element and is composed of a second rotating axis that is disposed perpendicular to the first rotating axis while enabling the rotating element to rotate about the second rotating axis so as to drive the x-ray tube and the swing element to move accordingly. In an embodiment, the rotating element is enabled to rotate for driving the x-ray tube to be oriented to an angle conforming to a line connecting the focal spot location to the focal point that is perpendicular to the first rotating axis, while the swing element drives the x-ray tube to swing for enabling the x-ray beam to be projected toward the focal point of the object to be imaged.

Accordingly, the present invention provides a loading mechanism for x-ray tube and a scanning system for 3D imaging, in that a digital tomosynthesis process in a longitudinal direction, in a translational direction, in an oblique direction or in a complex direction under a limited angle can be performed by the use of the first rotating axis of the swing element and the second roatating axis of the rotating element. In addition, as the focal spot location in the x-ray tube is defined to be the location where the x-ray beam is generated while also is the perpendicular position of the first rotating axis of the swing element to the second rotating axis of the rotating element as the first rotating axis is disposed passing through the focal spot location. Thereby, the focal spot location can be used as the origin for the x-ray projection as well as the origin of the moving of the swing element and the rotating element. Consequently, the origin of the x-ray as well as the vector thereof can be defined according to the position of the loading mechanism for x-ray tube and the positioning of the two rotating axes, so that as the degree of difficulty of the 3D spatial orientation is reduced by the aforesaid loading mechanism for x-ray tube, the resulting image reconstruction algorithm can be simplified for increasing the feasibility and applicability of a digital tomosynthesis process in a complex direction.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein:

FIG. 3 is a schematic diagram showing a scanning system for 3D imaging according to the present invention.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
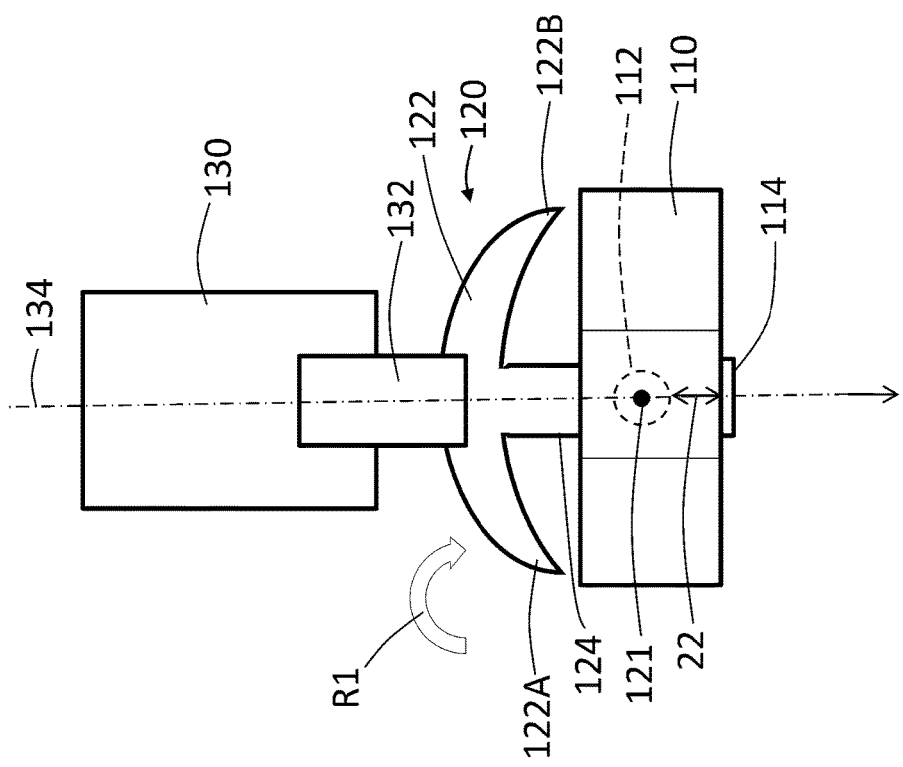
FIG. 1 is a schematic diagram showing a loading mechanism for x-ray tube according to the present invention.
Figure 2:
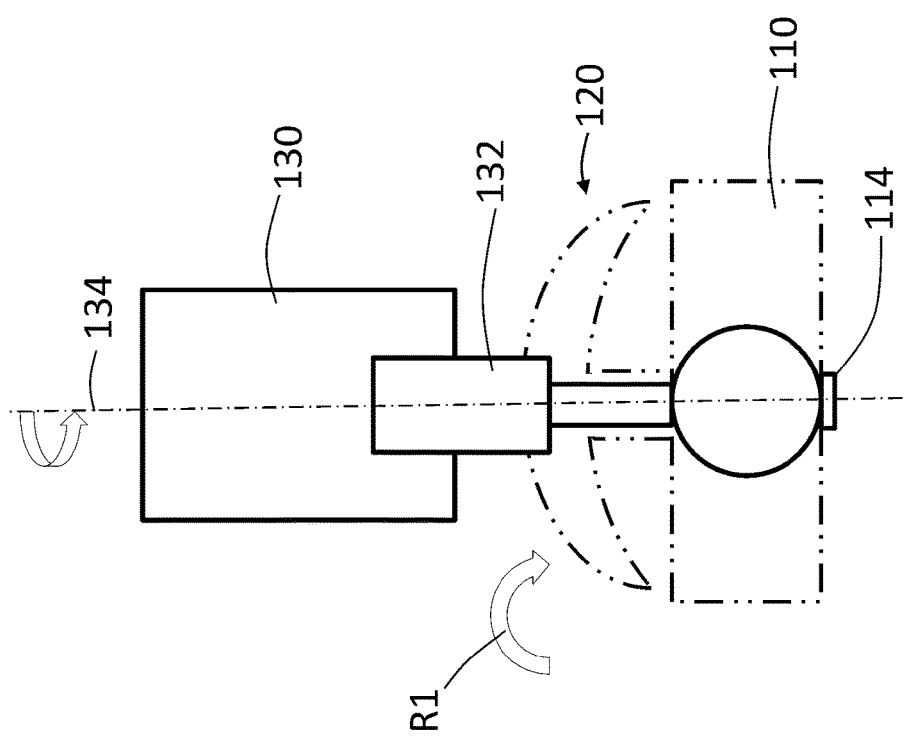
FIG. 2 is another schematic view of the loading mechanism for x-ray tub of FIG. 1 in another viewing angle.

Please refer to FIG. 1 and FIG. 2, which is a schematic diagram showing a loading mechanism for x-ray tube according to the present invention, and another schematic view of the loading mechanism for x-ray tub of FIG. 1 in another viewing angle.

In this embodiment, the loading mechanism for x-ray tube 100 includes an x-ray tube 110, a swing element 120 and a rotating element 130, in which the swing element 120 is coupled to the x-ray tube 110, and the rotating element 130 is coupled to the swing element 120.

The x-ray tube is substantially a cylinder-shaped object, which is formed with a focal spot location 112 and an x-ray opening 114 in a manner that the focal spot location 112 is related to a position where an x-ray beam is generated while the x-ray opening 114 is located for allowing the x-ray beam to travel therethrough.

The focal spot location 112 is disposed inside the x-ray tube 110 at a position neighboring to the x-ray opening 114. As shown in FIG. 1, the focal spot location 112 is disposed at the middle of the x-ray tube 110. However, the focal spot location 112 can be disposed at other positions inside the x-ray tube 110, i.e. it can be arranged slightly toward the left end or right end thereof. Nevertheless, the focal spot location 112 can be disposed at any position inside the x-ray tube 110 in the present embodiment.

In addition, the swing element 120 includes a first rotating axis 121, and the first rotating axis 121 is disposed perpendicular to the extension of the optical axis 22 of the x-ray beam, while the optical axis 22 is defined to be a line connecting the focal spot location 112 and the center of the x-ray opening 114, and the first rotating axis 121 is disposed passing through the focal spot location 112.

Specifically, the swing element 120 further includes a component with an arc-shaped fringe 122 and a connecting component 124, in which the component with an arc-shaped fringe 122 is connected to the connecting component 124 while the connecting component 124 is fixedly connected to the x-ray tube 110, and the arc of the component with an arc-shaped fringe 122 is further formed with a first end 122A and an opposing second end 122B.

The component with an arc-shaped fringe 122 is movably disposed at an end 132 of the rotation element 130, by that the component with an arc-shaped fringe 122 of the swing element 120 is enabled to rotate around first rotating axis 121 while centering to the focal spot location 112 for enabling the x-ray tube 110 to swing within a limit swing range R1. It is noted that the component with arc-shape fringe 122 has a first end 122A and an opposing second end 122B that are provided for defining the limit swing range R1 to be limited between the two ends 122A and 122B. Thereby, the component with arc-shape fringe 122 is movably attached to the end 132 of the rotation element 130 while enabling the x-ray tube 110 to swing accordingly.

Mechanically, the swing element 120 can be formed as a component with arc-shaped rack for example. In this embodiment. The swing element is substantially an arc-shaped gear that is fixed to the x-ray tube 110. Thereby, when the arc-shaped gear 120 is driven to rotate around first rotating axis 121, the x-ray tube 110 is enabled to swing conforming to the contour of the arc-shape gear 120 within the limit swing range R1. Despite the swing element is designed to be a gear, but it is not limited thereby. In other embodiments, the swing element 120 can be an assembly selected from the group consisting of: an assembly of a timing pulley and a lead screw, and an assembly of a worm and a worm wheel.

In addition, by attaching a magnetic component on the swing element 120 and correspondingly attaching an electromagnetic component on the rotating element 130, the present invention adopts a magnetic transmission mechanism for driving the x-ray tube to move. That is, operationally, when a control signal is issued for changing the magnetic flux of the electromagnetic component and consequently changing and adjusting the magnetic attraction/repulsion between the electromagnetic component and the magnetic component, the relative positioning between the swing element and the rotating element is changed accordingly and thus the x-ray tube 110 can be enabled to swing according to the relative positioning between the swing element and the rotating element.

It is noted that the component with an arc-shaped fringe 122 can be formed into a shape selected from the group consisting of: a circular shape, a semicircular shape, an oval shape, a sector-shape shape, and a shape with curved contour. However, it is not limited thereby, but can be a part with a contour capable of enabling the x-ray tube to swing within the limit swing range R1. Moreover, the rotating element 130 is composed of a second rotating axis 134 that is disposed perpendicular to the first rotating axis 121 and passing through the focal spot location 112.

Thereby, the rotating element 130 can be driven to rotate about the second rotating axis 134 so as to drive the x-ray tube 110 and the swing element 120 to move accordingly Please refer to FIG. 3, which is a schematic diagram showing a scanning system for 3D imaging according to the present invention.

In this embodiment, the scanning system for 3D imaging 50 includes: an imaging table 52, at least one at least one loading mechanism for x-ray tube 100 and a movable unit 54. It is noted that each of the at least one loading mechanism for x-ray tube 100 is the loading mechanism shown in FIG. 1 and FIG. 2.

The imaging table 52 is provided for supporting an object to be imaged 60 while the object 60 is defined with a focal point 62. In this embodiment, the object is a human body.

The movable unit 54 is disposed connected to the loading mechanism for x-ray tube 100. In an embodiment, the movable unit 54 is substantially a mechanical structure capable of moving the loading mechanism for x-ray tube 100 to an imaging position on the imaging table 52 for preparing the object 60 to be scanned.

In an embodiment, the rotating element 130 is enabled to rotate for driving the x-ray tube 110 to be oriented to an angle conforming to a line connecting the focal spot location 112 to the focal point 62 that is perpendicular to the first rotating axis 112, while the swing element 120 drives the x-ray tube 110 to swing for enabling the x-ray beam to be projected toward the focal point 62 of the object 60.

To sum up, the present invention provides a loading mechanism for x-ray tube and a scanning system for 3D imaging, in that a digital tomosynthesis process in a longitudinal direction, in a translational direction, in an oblique direction or in a complex direction under a limited angle can be performed by the use of the first rotating axis of the swing element and the second roatating axis of the rotating element. In addition, as the focal spot location in the x-ray tube is defined to be the location where the x-ray beam is generated while also is the perpendicular position of the first rotating axis of the swing element to the second rotating axis of the rotating element as the first rotating axis is disposed passing through the focal spot location. Thereby, the focal spot location can be used as the origin for the x-ray projection as well as the origin of the moving of the swing element and the rotating element. Consequently, the origin of the x-ray as well as the vector thereof can be defined according to the position of the loading mechanism for x-ray tube and the positioning of the two rotating axes, so that as the degree of difficulty of the 3D spatial orientation is reduced by the aforesaid loading mechanism for x-ray tube, the resulting image reconstruction algorithm can be simplified for increasing the feasibility and applicability of a digital tomosynthesis process in a complex direction.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A loading mechanism for x-ray tube, comprising:
an x-ray tube, composed of a focal spot location and an x-ray opening in a manner that the focal spot location is related to a position where an x-ray beam is generated while the x-ray opening is located for allowing the x-ray beam to travel therethrough;
a swing element, coupled to the x-ray tube and being composed of a first rotating axis in a manner that the first rotating axis is arranged passing through the focal spot location for allowing the swing element to rotate around first rotating axis while centering to the focal spot location and thus enabling the x-ray tube to swing within a limit swing range; and
a rotating element, connected to the swing element and being composed of a second rotating axis that is disposed perpendicular to the first rotating axis for enabling the rotating element to rotate about the second rotating axis so as to drive the x-ray tube and the swing element to move accordingly.

2. The loading mechanism for x-ray tube of claim 1, wherein the first rotating axis is disposed perpendicular to the extension of the optical axis of the x-ray beam, while the optical axis is defined to be a line connecting the focal spot location and the center of the x-ray opening.

3. The loading mechanism for x-ray tube of claim 1, wherein the second rotating axis is disposed passing through the focal spot location.

4. The loading mechanism for x-ray tube of claim 1, wherein the swing element further includes a component with an arc-shaped fringe; and the arc-shape fringe has a first end and an opposing second end that are provided for defining the limit swing range to be limited between the two ends.

5. The loading mechanism for x-ray tube of claim 4, wherein the component with an arc-shaped fringe is formed into a shape selected from the group consisting of: a circular shape, a semicircular shape, an oval shape, a sector-shape shape, and a shape with curved contour.

6. The loading mechanism for x-ray tube of claim 1, wherein the swing element further includes a component with a fringe formed with arc-shaped rack.

7. The loading mechanism for x-ray tube of claim 1, wherein the swing element further includes an assembly selected from the group consisting of: an assembly of a timing pulley and a lead screw, and an assembly of a worm and a worm wheel.

8. The loading mechanism for x-ray tube of claim 1, wherein each of the swing element and the rotating element includes a magnetic component and an electromagnetic component.

9. A scanning system for 3D imaging, comprising:
an imaging table, provided for supporting an object to be imaged while the object is defined with a focal point; and
at least one loading mechanism for x-ray tube, each including an x-ray tube, a swing element and a rotating element.
wherein, the x-ray tube includes a focal spot location and an x-ray opening, and the focal spot location is related to a position where an x-ray beam is generated while the x-ray opening is located for allowing the x-ray beam to travel therethrough; the swing element is coupled to the x-ray tube and is composed of a first rotating axis in a manner that the first rotating axis is arranged passing through the focal spot location for allowing the swing element to rotate around first rotating axis while centering to the focal spot location and thus enabling the x-ray tube to swing within a limit swing range; the rotating element is connected to the swing element and is composed of a second rotating axis that is disposed perpendicular to the first rotating axis for enabling the rotating element to rotate about the second rotating axis so as to drive the x-ray tube and the swing element to move accordingly; and the rotating element is enabled to rotate for driving the x-ray tube to be oriented to an angle conforming to a line connecting the focal spot location to the focal point that is perpendicular to the first rotating axis, while the swing element drives the x-ray tube to swing for enabling the x-ray beam to be projected toward the focal point of the object to be imaged.

10. The scanning system for 3D imaging of claim 9, wherein the first rotating axis is disposed perpendicular to the extension of the optical axis of the x-ray beam, while the optical axis is defined to be a line connecting the focal spot location and the center of the x-ray opening.

11. The scanning system for 3D imaging of claim 9, wherein the second rotating axis is disposed passing through the focal spot location.

12. The scanning system for 3D imaging of claim 9, wherein the swing element further includes a component with an arc-shaped fringe; and the arc-shape fringe has a first end and an opposing second end that are provided for defining the limit swing range to be limited between the two ends.

13. The scanning system for 3D imaging of claim 12, wherein the component with an arc-shaped fringe is formed into a shape selected from the group consisting of: a circular shape, a semicircular shape, an oval shape, a sector-shape shape, and a shape with curved contour.

14. The scanning system for 3D imaging of claim 9, wherein swing element further includes a component with a fringe formed with arc-shaped rack.

15. The scanning system for 3D imaging of claim 9, wherein the swing element further includes an assembly selected from the group consisting of: an assembly of a timing pulley and a lead screw, and an assembly of a worm and a worm wheel.

16. The scanning system for 3D imaging of claim 9, wherein each of the swing element and the rotating element includes a magnetic component and an electromagnetic component.

* * * * *